United States Patent [19]

Iversen et al.

[11] Patent Number: 4,803,029
[45] Date of Patent: Feb. 7, 1989

[54] PROCESS FOR MANUFACTURING AN EXPANDABLE MEMBER

[75] Inventors: Alfred A. Iversen, Wayzana; William Eastman, Hopkins, both of Minn.

[73] Assignee: PMT Corporation, Chanhassen, Minn.

[21] Appl. No.: 823,369

[22] Filed: Jan. 28, 1986

[51] Int. Cl.⁴ .............................................. B29C 43/18
[52] U.S. Cl. .................................... 264/264; 156/289; 156/290; 264/279.1; 264/320
[58] Field of Search ............ 264/134, 264, 325, 328.2, 264/130, 338; 249/112, 115, 114 R; 156/289, 290

[56] References Cited

U.S. PATENT DOCUMENTS

| | | | |
|---|---|---|---|
| 1,152,838 | 9/1915 | Price | 264/130 |
| 1,591,767 | 7/1926 | Maynard | 264/130 |
| 1,625,810 | 4/1927 | Krichbaum | 264/264 X |
| 1,970,802 | 8/1934 | Johnson | 264/264 X |
| 1,970,803 | 8/1934 | Johnson | 156/289 X |
| 2,269,342 | 1/1942 | Johnson | 156/289 X |
| 2,569,151 | 9/1951 | Coffey | 264/130 |
| 3,098,779 | 7/1963 | Cox | 264/264 X |
| 3,149,017 | 9/1964 | Ehrreich et al. | 156/289 X |
| 3,335,045 | 8/1967 | Post | 156/289 |
| 3,452,756 | 7/1969 | Harauteneian | 264/264 X |
| 3,595,950 | 7/1971 | Mezynski | 264/130 |
| 3,761,047 | 9/1973 | Mao | 249/115 |
| 4,112,041 | 9/1978 | Lonseth et al. | 264/263 |
| 4,288,058 | 9/1981 | Inman | 249/114 R X |
| 4,347,205 | 8/1982 | Stewart | 264/130 |

FOREIGN PATENT DOCUMENTS

| | | | |
|---|---|---|---|
| 212550 | 1/1957 | Australia | 264/134 |
| 174460 | 7/1921 | United Kingdom | 264/264 |
| 544905 | 2/1942 | United Kingdom | 264/264 |
| 691997 | 5/1953 | United Kingdom | 264/264 |

Primary Examiner—Jeffery Thurlow
Assistant Examiner—Leo B. Tentoni
Attorney, Agent, or Firm—Hugh D. Jaeger

[57] ABSTRACT

A process for manufacturing an expandable member such as a tissue expander or like product for use in plastic, reconstructive, and other surgery. A compression mold with a desired initial, predetermined geometrical configuration shape is filled partially with a layer of unvulcanized flexible material, such as silicone, a thin layer of Teflon or like non-stick substance, and followed by another layer of unvulcanized material. The Teflon is "sandwiched" between the unvulcanized material and cured in an oven or by other suitable means. The non-stick material provides a separation region for subsequent expansion by injection of suitable material, air, fluid, etc. The non-stick material can be shaped to provide expansion only in the desired regions. Single, multiple, or overlapped layers of non-stick material may be employed to manufacture a variety of expandable products in the fields of medicine, surgery, consumer and industrial applications.

3 Claims, 9 Drawing Sheets

PROCESS FOR MANUFACTURING AN EXPANDABLE MEMBER

BACKGROUND OF THE INVENTION

1. Field of the Invention

The present invention relates to a process of manufacturing an expandable member such as a tissue expander and other medical and surgical products, such as used in plastic, reconstructive, and other surgery. Such products, as tissue expanders are made from silicone or other suitable pliable material with an intended non-stick member, and have a chamber which can be filled with fluid after the expander is positioned in the appropriate surgical location.

2. Description of the Prior Art

Prior art tissue expanders have been fabricated by coating a mandrel and after curing, removing the formed product. Subsequent operations include the gluing of tubing in place. Such devices have been prone to fail by breaking at the glued seam, and allowing the fluid to leak from the expander into the adjacent tissue. This not only causes the loss of expansion but can have harmful effects on the patient. Some expanders have been made without seams in a fashion similar to balloons. Such expanders lack dimension stability during insertion, making such very difficult to properly position in the tissue. This same lack of dimensional stability in like products tends to cause such expanders to expand in typical balloon-like fashion, which seldom is in the desired shape.

This invention provides a tissue expander with dimensional stability and reliability of a one-piece assembly having a thin layer of non-sticking material imbedded about the region where expandability is desired.

SUMMARY OF THE INVENTION

The general purpose of this invention is to provide a process of manufacturing an expandable member of a seamless, relatively low profile, tissue expander or other like expandable product, which can be accurately positioned with minimum trauma in existing tissue. The tissue expander is preferably fabricated by a molding process in which a thin layer of non-stick material, having a general outline corresponding to the area of desired expansion, is positioned within a mold. Silicone or other suitable pliable material is placed within the mold and cured. The resulting article will expand along the non-stick surfaces when it is filled with a fluid or otherwise inflated.

The non-stick material is typically fluorocarbon material such as Teflon (Trademark of the E. I. Du Pont Co.) a name for polytetrafluoroethylene and the copolymer tetrafluoroethylene/hexafluoropropylene, hereinafter referred to in the specification and claims as either Teflon or PTFE. not more than about a few thousanths of an inch thick. It may be a single layer, multiple layers or overlapping layers. While it will be flat in most circumstances, it can be tubular or of other geometrical form, or a combination of forms as necessary. The non-stick layer is preferably connected to a valve or other port adapted to allow the insertion of fluid or gas to expand the device. The valve can even be other non-stick material positioned over a part of a tube in the chamber. The process for manufacturing and fabricating the device can accommodate the inclusion of materials such as Dacron (Trademark of the E. I. Du Pont Co.) a name for polyethylene terephthalate, webbing about or in one or more surfaces to provide for expansion only at predetermined areas.

A significant aspect and feature of the present invention is to provide a method for fabricating a seamless tissue expander, or other product, which has an essentially flat shape to minimize trauma to the skin and the adjacent tissue during insertion and subsequent expansion.

Another significant aspect and feature of the present invention is to provide a method for fabricating a seamless tissue expander which contains a sheet, or other shape, of non-stick material to provide for parting surfaces when the device is expanded by the insertion of gas or fluid.

A further significant aspect and feature of the present invention is to manufacture an expandable member with an internal non-stick member.

Having thus described embodiments of this invention, it is an object hereof to provide a process for manufacturing and fabricating a one-piece molded tissue expander or like expandable product having a non-stick material embedded therein, providing parting surfaces for expansion.

Another object of this invention is to provide a method for fabricating a flat, one-piece tissue expander having a non-stick member embedded therein for providing parting surfaces of expansion.

A further object of this invention is to provide a method for fabricating a one-piece, molded tissue expander having a non-stick member and additional expansion controlling material embedded therein.

DESCRIPTION OF THE PREFERRED EMBODIMENTS

Figure 1:
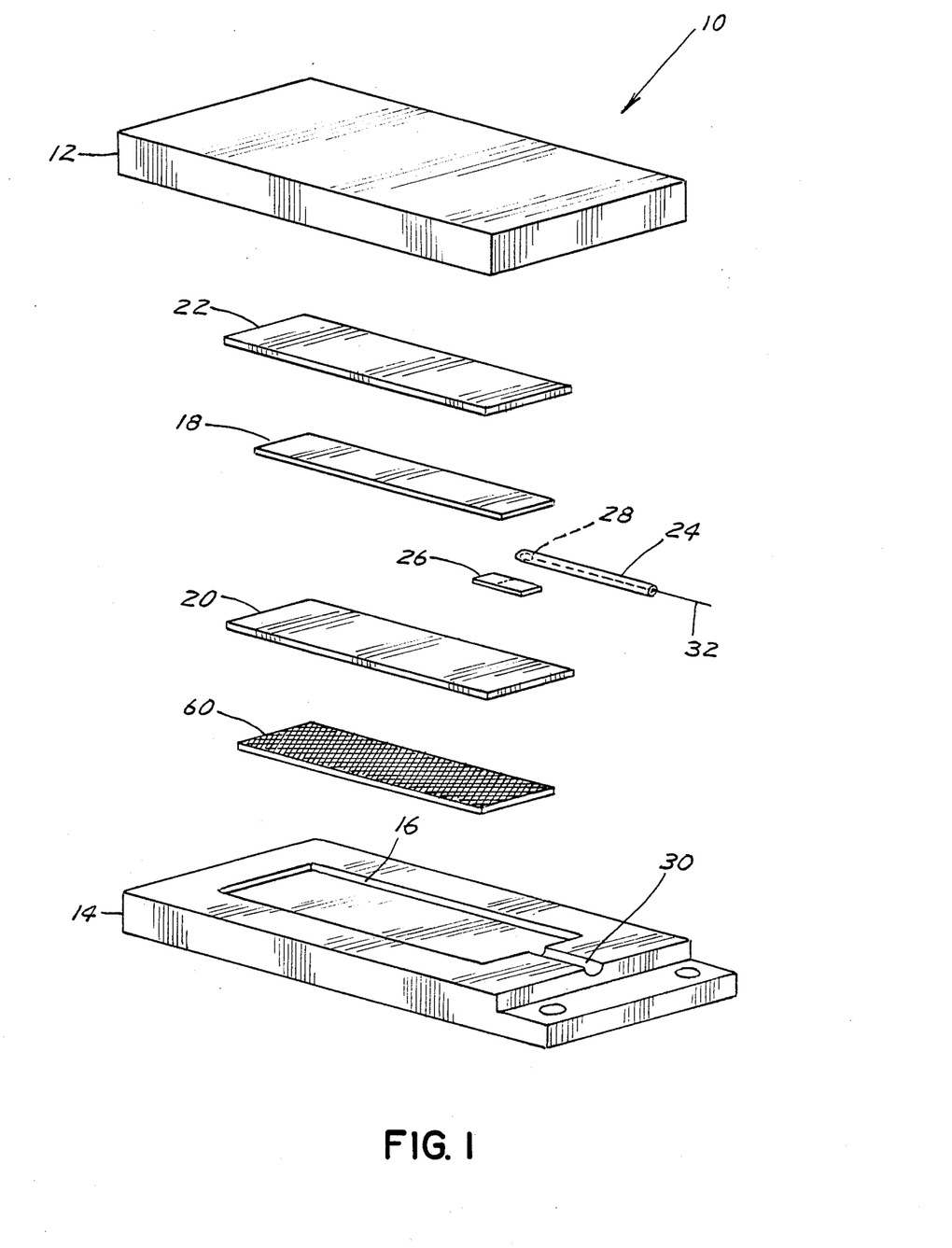
FIG. 1 is a schematic showing of a mold cavity with the non-sticking material positioned centrally in the mold cavity filled with material prior to curing for performing the process to fabricate a tissue expander.
Figure 2A:
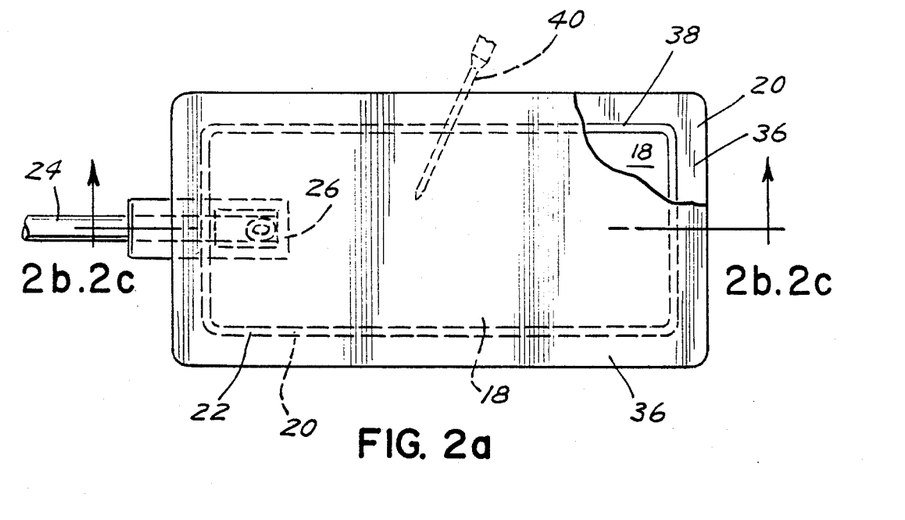
FIGS. 2a–2c illustrates a series of views showing the position of the non-sticking material in the relaxed and expanded states of a tissue expander where the process includes a single element of non-sticking material.

Other objects and many of the attendant advantages of this invention will be readily appreciated as the same becomes better understood by reference to the following detailed description when considered in connection with the accompanying drawings, in which like reference numerals designate like parts through the FIGURES thereof and wherein:

FIG. 1 illustrates a perspective exploded view of a mold for fabricating and manufacturing an expandable member such as a tissue expander. The mold 10 includes an upper section 12 and a lower section 14 including cavity portion 16. The mold sections are shown in the open position, with a sheet 18 of non-sticking flat like material, such as fluorocarbon Teflon, positioned centrally between the inner surfaces of material 20 and 22, such as unvulcanized silicone rubber. Other nonsticking substances could be used such as powder, liquid, and can even include fluorocarbons to enhance the non-sticking. A silicone or like tube 24 including a flap of non-stick material 26 over the bias cut outlet part 28 positions at inlet 30 of the mold 14. Optionally, in lieu of flap 26, two sheets 18 of Teflon material can be utilized and the two sheets would further act as a valve. The sheets would not have to be identical in size. A wire or stylet 32 is engaged within the tube to the approximate end of the outlet port 28 for preventing backward flow of material into the orifice 28 of the tube and compression of the tube during curing. The sheet 18 is a smaller cross sectional area the sheets 20 and 22 which are substantially equal in cross sectional area. The mold sections 12 and 14 are brought together under pressure at an elevated temperature over a time period and the elastomeric materials 20 and 22 are cured through the application of pressure and heat over time or by some other suitable known process. When the elastomeric materials 20 and 22 are completely cured, the mold cavity halves 12 and 14 are separated, and a tissue expander 34 of FIG. 2 is removed. A Dacron or other reinforcement member 60 can be used in the molding process for expander stability as later discussed in detail in FIGS. 4 and 5.

FIG. 1 shows the details of the mold by way of example and for purposes of illustration only. Injection molding would also be another way to fill the mold with elastomeric material in the unvulcanized or uncured state. If injection molding is used, it would be possible to inject the elastomeric material from opposite sides of the mold while positioning the non-sticking material in the center of the cavity. By controlling the relative flow rates from the respective sides, the elastomeric material could be thicker adjacent to one surface of the mold cavity or thinner adjacent to the other. The significance of this will be discussed in more detail at a later point.

In some cases, it may be desirable to coat the non-sticking material 18 with a layer of elastomeric material, and partially cure the elastomeric coating prior to placing the non-sticking material in the mold. This would assist in holding the non-sticking material in the proper position within the mold cavity.

Although the preferred embodiment of the process contemplates curing the elastomeric material to completion while the mold is maintained in the closed position, in some circumstances the elastomer may have sufficient dimensional stability in the partially cured condition to permit the expander to be withdrawn from the mold and curing completed outside the mold.

While the non-sticking material 18 is preferably fluorocarbon Teflon because of its inert nature, nonsticking characteristics, and resistance to the temperatures used in the curing phase of the process, other like materials may also be used. Further, while thin sheets, in the order of 0.01 to 0.0001 are preferred, there may be occasions where a powder, liquid, or composite non-stick material is used in lieu of the Teflon. In the case of composite materials, a Teflon coating is preferred because of its inert nature, nonsticking characteristics and resistance to high temperatures.

FIG. 2a illustrates a plan view of a tissue expander 34 produced from the mold of FIG. 1. The now cured continuously molded elastomeric material 36 contains the sheet 18 of non-sticking material. Sheet 18 is generally flat of a smaller cross sectional area through the expander and has a geometrical outline corresponding to the physical outline of the desired region of expansion of the expander 34.

Figure 2B:
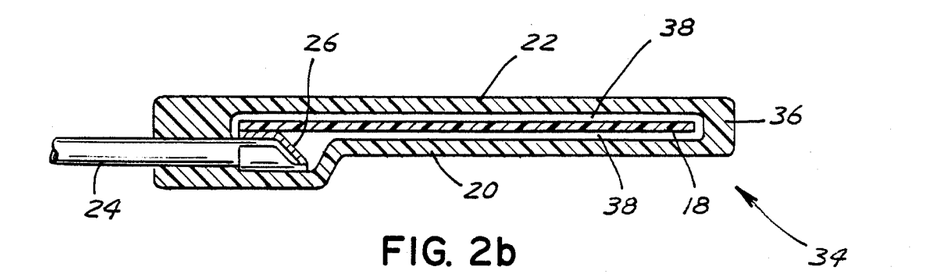

FIG. 2b is a sectional view of the tissue expander 34 taken along the line 2B—2B of FIG. 2a. This view shows the expander 34 in the relaxed or unexpanded condition. The cured elastomeric material 36 surrounds the non-sticking material 18 forming a chamber 38. A mold line 37 is also shown. In this low profile condition, the tissue expander is particularly well suited to be positioned in the tissue to be expanded. In the unexpanded condition, the tissue expander is relatively small and has sufficient dimensional stability or "body" to allow the expander 34 to be slid beneath the skin through an incision of least dimensions, and placed in final position through external surgical manipulation.

Once in place, a needle 40 affixes to a suitable syringe and may be used to inject a suitable liquid, gas, or other material through the wall of the expander or it may be expanded through the integral bias cut tube 24 and past the Teflon flap valve 26 into the regions of the boundary between the elastomeric materials 20 and 22 and the non-sticking material 18. The pressure of the injectable fluid causes the elastomeric material to expand outwardly, about and separating by pulling away from the non-sticking material 18. Back pressure against Teflon valve flap 26 seals the tube 26 end maintaining pressure within the chamber 38.

Figure 2C:
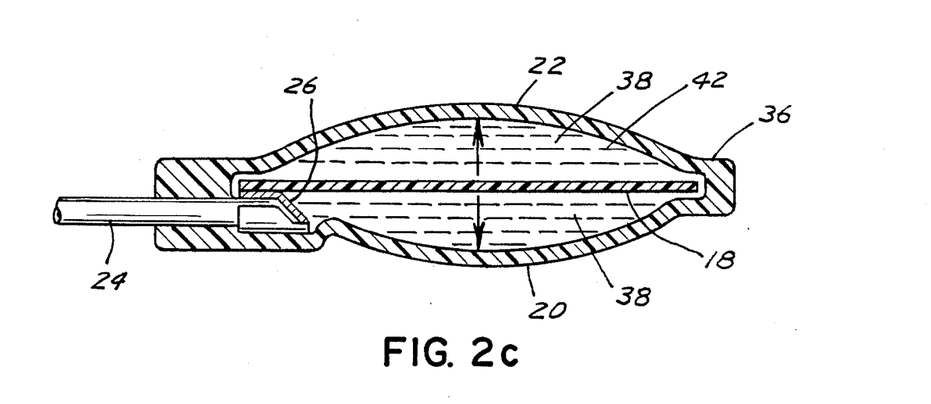

FIG. 2c is a sectional view along the line 2c—2c of FIG. 2a after the expander 34 has been filled with an expander material 42 comprised of liquid, gas or other suitable materials. Although other suitable materials exist, a saline solution is preferred because of its compatibility with living tissue should the expander develop a leak due to external compression injury, etc. which is very unlikely. Injection of a sufficient amount of material 42 causes the extension of the walls 20 and 22 of the expander on both sides of the non-sticking material 18 to provide expansion. Such expansion is the result of the nonsticking material 18 being positioned between the major surfaces of the materials 20 and 22.

Figure 3A:
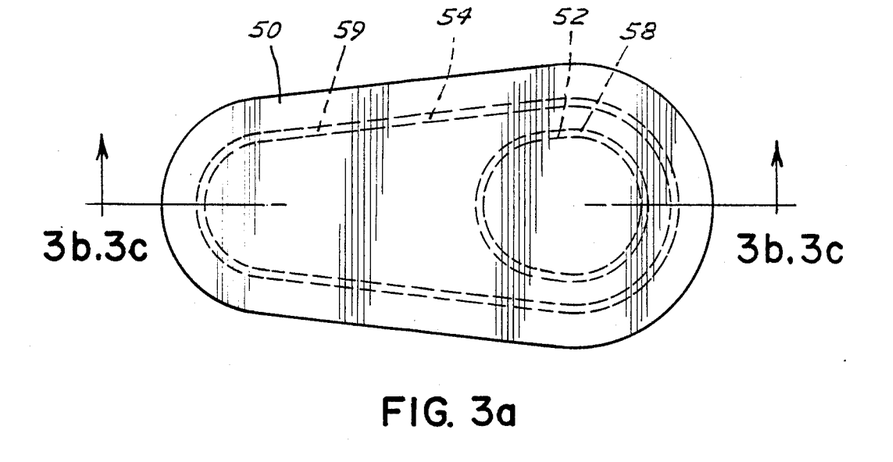
FIGS. 3a–3c illustrates a series of views including cross-sectional views, showing the position of the non-sticking material in the relaxed and expanded states where the process includes a plurality of nonsticking elements.
Figure 3B:
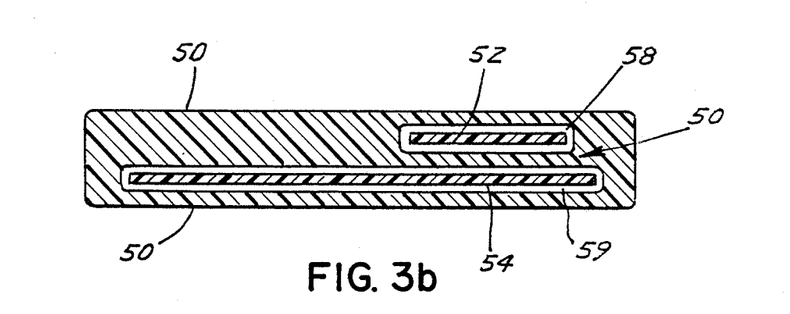
Figure 3C:
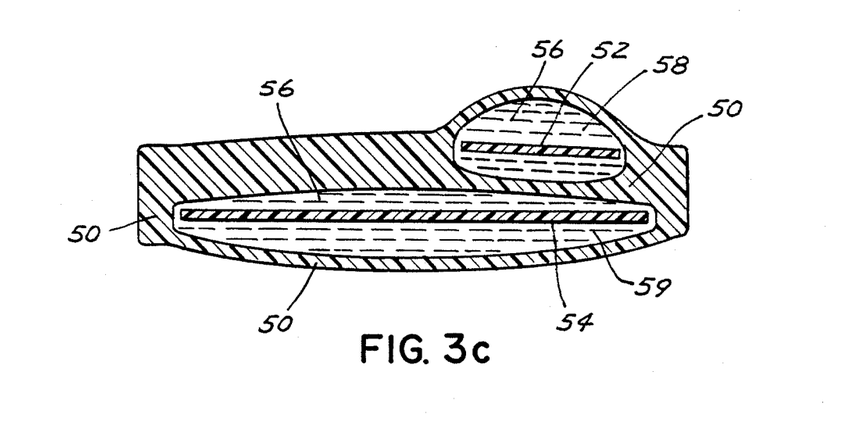

FIGS. 3a–3c illustrate that there are situations where unsymmetrical expansion is the desired preferred mode and alternative embodiments such as shown in FIG. 3 are fabricated as an alternative embodiment. The plan view of FIG. 3a shows the cured elastomeric material 50 which contains more than one sheet of nonsticking material. Two sheets 52 and 54 are positioned in an overlapping relationship in this example for purposes of illustration but not to be construed as limiting of the present invention.

FIG. 3b illustrates a sectional view taken along the line 3b—3b of FIG. 3b, showing the expander in the relaxed or unexpanded condition. The non-sticking elements 52 and 54 are generally parallel to each other, and separated by a layer of elastomeric material 50. In this particular embodiment, there is no connection between elements 52 and 54. The separation between the elements 52 and 54 can be obtained by coating the abutting surfaces with the elastomeric material and at least partially curing it prior to inserting the elements into the mold. Alternatively, other methods can be used to achieve the desired separation.

Expansion of this tissue expander of the embodiment assumes the shape of the sectional view of FIG. 3c, taken along the line 3c—3c of FIG. 3a. Two injections must be made with suitable material 56, one into the chamber region 58 surrounding element 52, and one into the chamber region 59 surrounding element 54 unless a common port is provided between the regions. This provides the advantageous result of being able to selectively control the expansion of the two areas encompassed by the respective elements. In this particular embodiment, the expansion of each chamber is still basically symmetrical although it can be seen that the expansion in the region of the element 52 is affected by the fact that it is closer to one wall of the mold surface than the other element 54, causing greater distension in that direction. In the alternative an inflation/expander tube with corresponding non-stick Teflon valve as illustrated in FIG. 2 can be installed at the left end of FIG. 3a–3c along with a passage tube, not illustrated, between chambers 56 and 58 for other means of inflation or expansion of the tissue expander illustrated in FIG. 3a–3c.

Figure 4A:
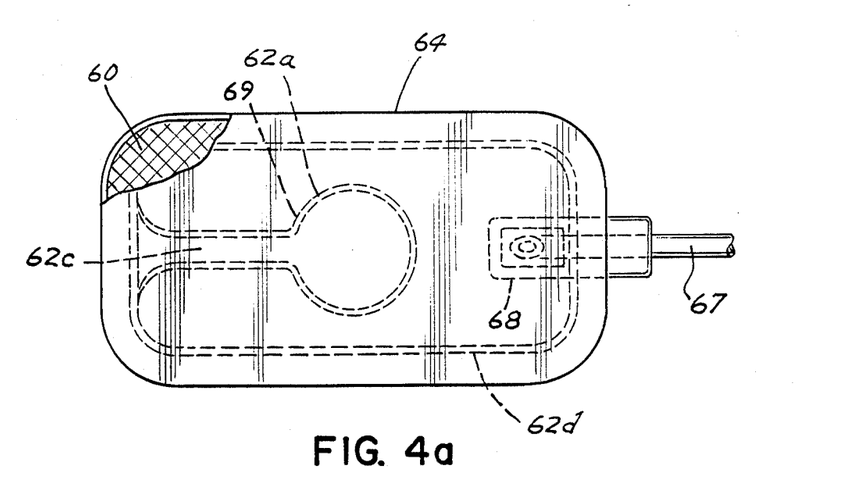
FIGS. 4a–4b illustrates a series of views including a cross-sectional view, showing the outline of the non-sticking material in the expanded state where the process includes non-sticking material in overlapping relationship.
Figure 4B:
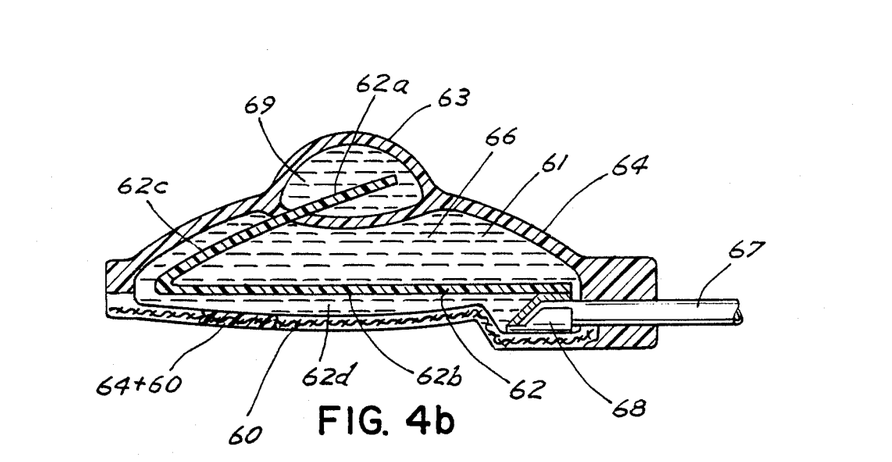

FIGS. 4a–4b illustrate partial cut away and cross-sectional embodiments of selective expansion. It has been determined advantageous to reinforce one wall of a tissue expander for some medical or other applications. The embodiment of FIG. 4 includes a reinforcement woven or like material 60 fabricated of Dacron, Teflon, Delrin, fluorocarbon or other suitable material positioned and imbedded within the mold cavity with the unvulcanized elastomeric material 64, and is shown in a small portion as 64 and 60 in the illustration but for clarity is shown as woven material otherwise throughout. The reinforcement material 60 can be precoated with unvulcanized elastomeric material and partially cured before placing it in the mold cavity or the reinforcement material can be placed between two layers unvulcanized elastometic material.

The reinforcement material 60 reduces the amount of expansion of the wall containing the reinforcement 60. Selective expansion of the upper expander 63 in the opposite direction can also be achieved by further folding a portion 62a of non-sticking element 62 back to overlap a portion of the surface of material 62. The overlapped portion 62a has an outline corresponding to the desired region of expansion and communicates with the major surface 62b of element 62 via a connecting portion 62c. The connecting portion 62c allows the expander to be filled with a single injection of expansion material 66 since injection of fluid into either the region of 62a or edge 62d causes the elastomeric material 64 to part from the entire surface, creating a communication channel along the connecting portion 62c. Integral bias cut tube 67 and Teflon valve member 68 provide for inflation or expansion and sealing of lower chamber 61 and the upper chamber 69 as previously discussed in FIG. 2.

Figure 5A:
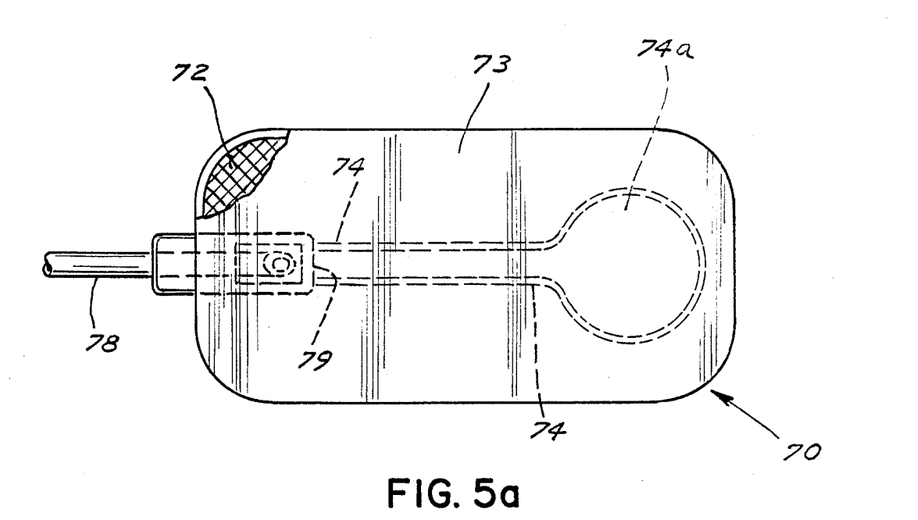
FIGS. 5a–5b illustrates a series of views including a cross-sectional view, showing the outline of the non-sticking material in the expanded state where the process includes non-sticking material having an irregular outline corresponding to the areas of desired expansion.
Figure 5B:
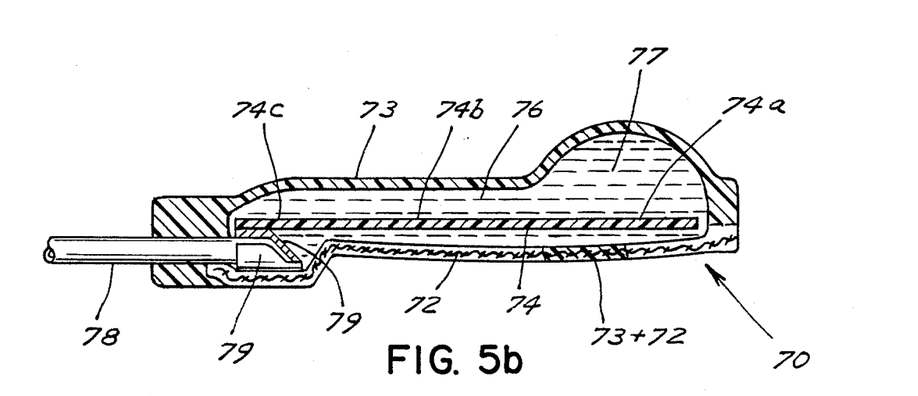

FIGS. 5a and 5b illustrate the embodiments of the expander 70, including a cross sectional view and also containing a reinforcing material 72 or other like material embedded in silicone and illustrated in part as 73 & 72 but for clarity is shown as woven material 72 otherwise throughout. Selective expansion is achieved by geometrical configuring the outline of non-sticking material 74 as shown in the dashed line of FIG. 5a. As shown in FIG. 5b, the primary expansion of the elastomeric material 73 occurs in the region of non-sticking material 74a, and region 74b can be used to provide a communication channel as well as for expansion allowing fluid or expansion material 16 to be injected at a location remote from the region of primary expansion, such as near non-sticking material region 74c via tube 78. Integral bias cut tube 78 and Teflon valve member 79 provide for inflation or expansion and sealing of the chamber 77 as previously discussed in FIG. 2.

Figure 6A:
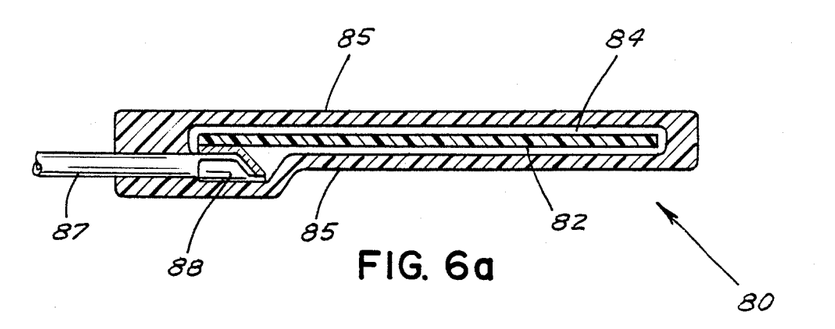
FIGS. 6a–6b illustrates cross-sectional views of a tissue expander in the relaxed and expanded states where the process positions the non-sticking material equidistant from the surface of the mold cavity.
Figure 6B:
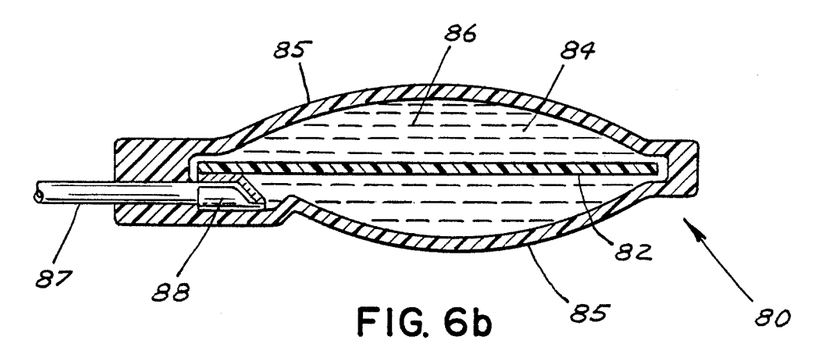

FIGS. 6a and 6b illustrate cross sectional views of the expander 80 where the process involves positioning the non-sticking material 82 essentially equidistant from the major surfaces of the mold cavity. The sectional view of FIG. 6a is taken along a line which bisects the major dimension of the expander 80 and shows the walls of the elastomeric material 85 to be substantially the same thickness. When the fluid expansion material 86 is injected into the expander cavity 84 through tube 87 or by a needle, not shown, the expander 80 takes on the form shown in FIG. 6b. It can be seen that the expansion is substantially symmetrical about the non-sticking material 82. That is, both walls distend about the same amount. Integral bias cut tube 87 and Teflon valve member 88 provide for inflation or expansion and sealing of the chamber 84 as previously discussed FIG. 2.

Figure 7A:
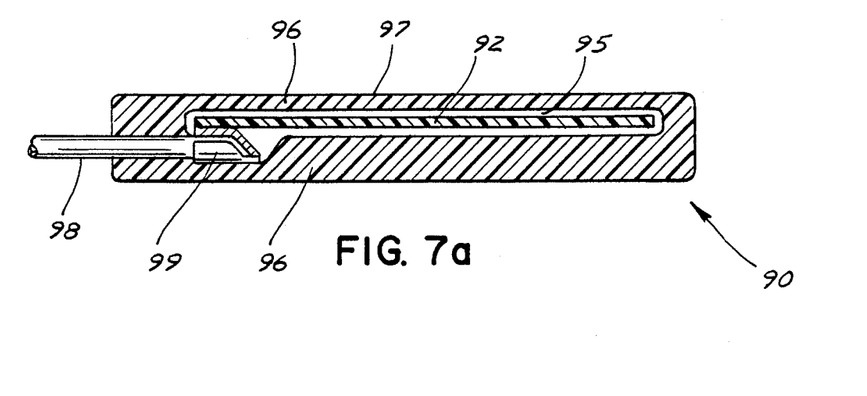
FIGS. 7a–7b illustrates cross-sectional views of a tissue expander in the relaxed and expanded states where the process positions the non-sticking material nearer to one surface of the mold cavity than the other surface.
Figure 7B:
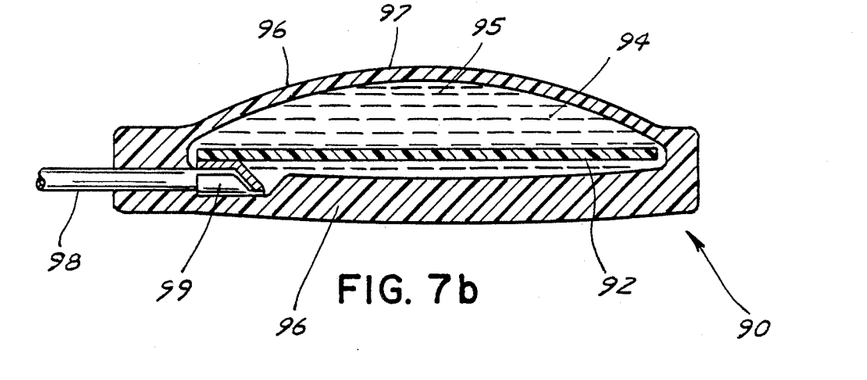

FIGS. 7a–7b illustrates cross sections of embodiment 90, an expander which provides for non-symmetrical expansion by positioning the non-sticking element closer to one surface of the mold than the other during the molding process; that is, a thickness differential between the wall materials. This results in a structure having a relaxed shape resembling the sectional view of FIG. 7a, taken along a line which bisects the major dimension of the expander similar to FIG. 6a. When the fluid expansion material 94 is injected into the chamber 95 through tube 98 or by a needle, not shown into the region where the surface of non-sticking element 92 abuts the elastomeric materials 96, expansion takes place as shown in FIG. 7b. It can be seen that the greatest expansion takes place in the direction of the thinner wall elastomer 97 which results from the differential positioning of the thickwall elastomer material 96 and the thinwall elastomer 97 in the mold during the molding process. Integral bias cut tube 98 and Teflon valve member 99 provide for inflation or expansion and sealing of the chamber 95 as previously discussed in FIG. 2.

Figures 8A, 8B:
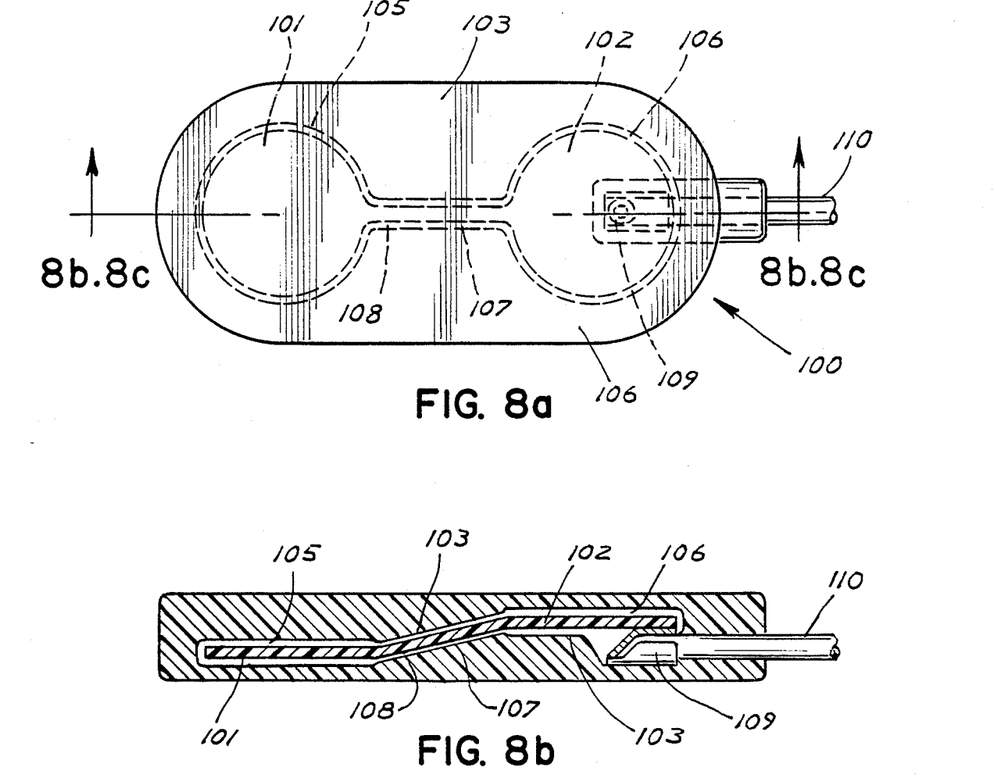
FIGS. 8a–8c illustrates a series of views including cross-sectional views of a tissue expander in the relaxed and expanded states where the process positions one piece of non-sticking material close to one surface of the mold cavity and another piece of non-sticking material close to the other surface of the mold cavity; and, FIGS. 9a–9c illustrates a series of views including cross-sectional views of a tissue expander in the relaxed and expanded states where the process includes non-sticking material in an overlapping relationship.
Figure 8C:
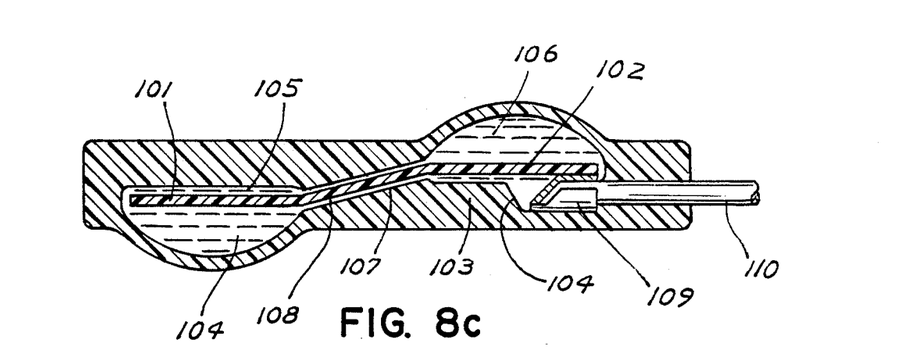

FIGS. 8a–8c shows embodiment 100, an expander, which can be used to provide selective expansions in opposite geometrical directions. As shown in FIG. 8a, a pair of non-sticking elements 101 and 102 are positioned within the elastomeric material 103. Non-stick element 101 is positioned close to one surface of the mold, and non-stick element 102 is positioned close to the other surface of the mold. This is illustrated in the sectional view of FIG. 8b taken along the line 8b—8b of FIG. 8a. When the fluid expansion material 107 is injected into chambers 105 and 106, expansion takes place as shown in FIG. 8c, non-sticking elements 101 and 102 are shown as continuous elements for communication between the cavities. It will be appreciated that it may be desirable to connect elements 101 and 102 within the passage 107 along with a small non-stick Teflon strip 108 as was done in the embodiment shown in FIG. 4. Again, differential material thickness is illustrated accordingly. Integral bias cut tube 110 and Teflon valve member 109 provide for inflation or expansion and sealing of chamber 106 and subsequent inflation or expansion of chamber 105 via passage 107 as previously discussed in FIG. 2. In the alternative an expander without passage 107 included can provide for different levels of expansion of each chamber individually by the use of an inflation needle injecting expansion material into the individual chamber 104 and 106.

Figure 9A:
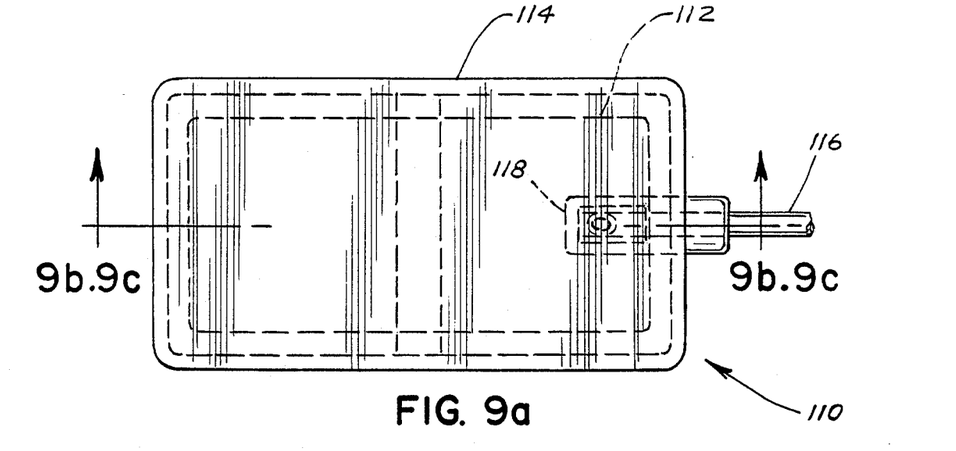
Figure 9B:
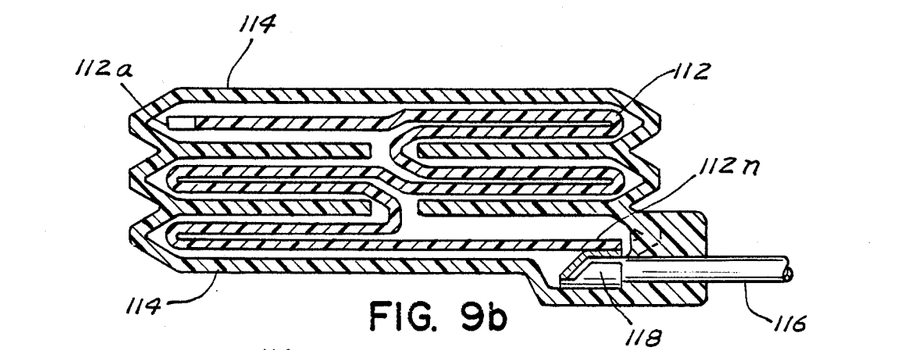
Figure 9C:
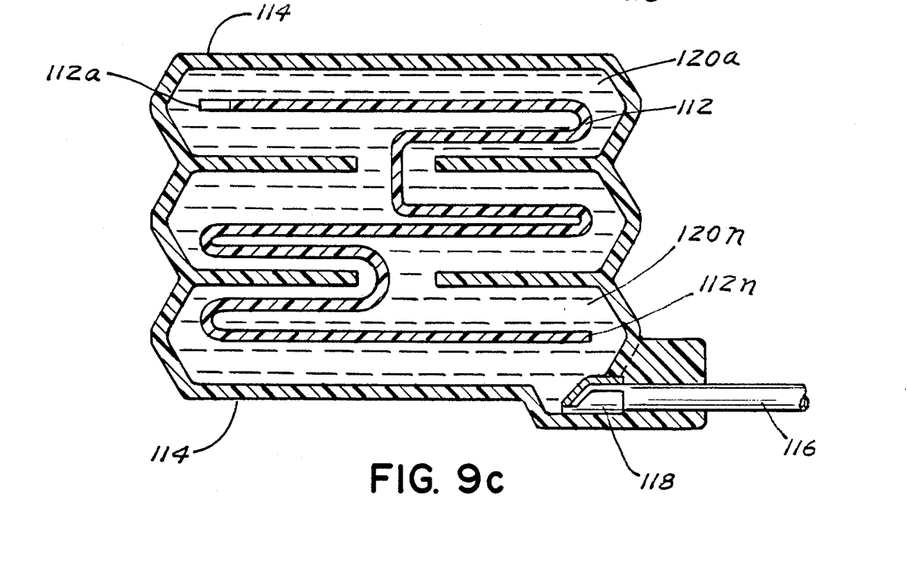

FIGS. 9a–9c illustrate embodiments 110, and expander, including cross sectional views where a great amount of expansion is required. The outline shown in FIG. 9a is arbitrary and any suitable shape may be employed. The non-sticking material 112 is surrounded by elastomeric material 114 as shown. The non-sticking material 112a–112n can include a plurality of layers as shown in FIG. 9b, a sectional view taken along the line 9b—9b of FIG. 9a. Expansion or inflation material introduced through integral bias cut tube 116 and Teflon valve member 118 provide for inflation and expansion in a greatly pronounced upward expansion in an accordion-like fashion as illustrated in FIG. 9c. Chambers 120a–120n are filled through the flap valve member 118 as previously discussed in FIG. 2. The non-sticking element 112 can take a generally serpentine shape, being folded back and forth several times to form a plurality of layers, or in the alternative it can be layered.

MODE OF OPERATION

FIG. 1 best illustrates the mode of operation for the process of manufacturing an expandable member such as a tissue expander or other like product. An unvulcanized silicone sheet 20 approximately 0.010"–0.030", by way of example, thick is placed over the lower mold section 14 which contains a predetermined shaped mold cavity 16 and a tube mold inlet 30 for accommodation of an inflation or expansion tube 24 which is placed later in the powers. A non-stick Teflon flapper valve element is positioned over the unvulcanized silicone sheet 20 in the area of the tube mold inlet 30. An inflation or expansion bias cut tube 24 is then placed over the flapper valve member 26 and the unvulcanized silicone layer 20. The non-stick flapper valve member is then bent back along the dotted line shown in the illustration and across the beveled end of the tube 24. The silicone layer 20, the folded over flapper valve member 26 and the tube 24 are then maneuvered downward into the tube mold inlet 30 and at the same time the unvulcanized silicone layer 20 is placed over mold cavity 16 of the lower mold member 14. Next the non-stick element 18 is placed in position centrally on top of element 20. A second sheet of 0.020 unvulcanized silicone 20 is next positioned over unvulcanized silicone layer 20, flapper valve 26 and tube 14. A stylet or piece of wire 32 is then inserted in open end of tube 24 extending to but not past the orifice 28 to prevent filling of the orifice 28 by heated expanding material, and to prevent closure of the tube passage due to the compression and heating of the mold and the contents therein. A 0.020" dacron mesh, reinforced unvulcanized silicone member 60, trimmed to fit inside of the mold cavity 16 with an expansion gap between its edge and the edge of the mold cavity 16, can be substituted for the lower unvulcanized silicone layer 20 when an expander with controlled expansion is the desired end result. When all the elements are in place on the mold any excess material past one eighth of an inch outwardly from the cavity 16 is trimmed off with a scalpel or other suitable means prior to compression and heating of the mold. The mold halves 12 and 14 are then compressed depending on the size of the expander, from 500 pounds per square inch to 4,000 pounds per square inch and heated from 250° F. to 500° F. for two to five minutes vulcanizing and curing elastomerically the edges of the top sheet 22 to the edges of the bottom sheet 20, or in the alternative edges of the reinforced sheet 60, with the Teflon non-stick sheet 18, bias cut tube 24 and Teflon non-stick flapper valve 26 between tube 24 is embedded elastomerically between the upper and lower sheets 22 and 20 or 60 providing for an airtight seal. For purposes of illustration and by way of example, the underside of mold top 12 is flat, resulting in a smooth topped expander but can be of another predetermined geometrical configuration for a differently shaped expander top side when desired. The expander is then removed from the mold, the mold flashing is then trimmed off of the exterior edge and stylet 32 is removed from the passage of the inflation/expansion tube 24.

While the previous embodiments utilize relatively flat sheets of non-sticking material, as shown, other shapes such as tubular may be used in particular circumstances. There may be circumstances where the nonsticking material is positioned in the mold cavity as a liquid, for example by spraying or injection. The nonsticking material may be suspended in a liquid for this purpose or be used in undiluted form. Such an approach might be desirable where the tissue expander must be very flexible, and even a very thin sheet of solid nonsticking material would prevent the proper use of the device. In other embodiments, the non-sticking material may be a coating applied to a structural element included in the expander for desired reasons.

When a sheet of fluorocarbon such as Teflon is used, the preferred thickness is in the range of 0.001 inches, ideally 0.0008. This will vary with the particular use of the tissue expander and thickness from 0.01 to 0.0001 can be employed.

It will be appreciated that the tissue expander of this invention, by way of example and for purposes of illustration only, has application to other surgical appliances, such as surgical balloons, extrusion catheters, and similar devices. Further, principles of manufacturing as disclosed are also applicable to fluid seals, balloons per se, and like expandable structures. The principle steps of the process are also applicable to consumer and recreation products, auto products such as air bags, inflatable toys, energy products, and industrial products.

We claim:
1. Process for manufacturing an expandable member comprising the steps:
   a. opening a mold with opposing like cavities and a port indentation;

b. positioning a first sheet of unvulcanized material in a first of said cavities;

c. positioning at least one sheet of non-stick material of a smaller area size than said first sheet of unvulcanized material;

d. positioning a like sheet of unvulcanized material in the other of said cavities;

e. positioning a port tube in said port indentation in between said unvulcanized materials and adjacent said sheet of nonstick material;

f. positioning a flap of non-stick material over a port end of said tube;

g. closing said mold; and, h. curing said unvulcanized material under pressure at an elevated temperature over time.

2. Process of claim 1 including steps of:

a. polyethylene terephthalate material affixed to one of said unvulcanized materials.

3. Process of claim 1 including the steps of:

a. polyethylene terephthalate material affixed to both of said unvulcanized materials.

* * * * *